United States Patent

MacKenzie et al.

[11] Patent Number: 5,846,965
[45] Date of Patent: Dec. 8, 1998

[54] 3-AZA AND 3-OXA PIPERIDONE TACHYKININ ANTAGONISTS

[75] Inventors: Alexander Roderick MacKenzie; Allan Patrick Marchington; Sandra Dora Meadows; Donald Stuart Middleton, all of Sandwich, United Kingdom

[73] Assignee: Pfizer Inc., New York, N.Y.

[21] Appl. No.: 788,001

[22] Filed: Jan. 24, 1997

[30] Foreign Application Priority Data

Jan. 27, 1996 [GB] United Kingdom .................. 9601680

[51] Int. Cl.⁶ ...................... A61K 31/395; C07D 243/08; C07D 403/14; C07D 205/04
[52] U.S. Cl. ........................ 514/210; 540/544; 540/575; 540/598; 540/601; 544/96; 544/121; 544/295; 544/316
[58] Field of Search ............................... 514/210; 544/96, 544/121, 295, 316; 540/544, 575, 598, 601

*Primary Examiner*—Mukund J. Shah
*Assistant Examiner*—Brenda Coleman
*Attorney, Agent, or Firm*—Peter C. Richardson; Paul H. Ginsburg; B. Timothy Creagan

[57] ABSTRACT

Compounds of the formula:

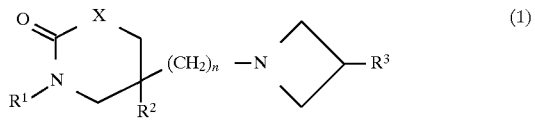

wherein:

X is O, NH or $NR^1$; $R^1$ is $C_1$–$C_6$ alkyl, $C_3$–$C_7$ cycloalkyl, $C_3$–$C_7$ cycloalkyl($C_1$–$C_4$)alkyl, aryl or aryl ($C_1$–$C_4$) alkyl; wherein the $C_1$–$C_6$ alkyl group is optionally substituted by fluorine and the $C_3$–$C_7$ cycloalkyl or $C_3$–$C_7$ cycloalkyl($C_1$–$C_4$ )alkyl group is optionally substituted in the cycloalkyl ring by up to two substituents each independently selected from halo, $C_1$–$C_4$ alkoxy or halo($C_1$–$C_4$)alkoxy; $R^2$ is phenyl optionally substituted with one or two halo substituents, indolyl or thienyl; $R^3$ is $NH_2$, $-NR^4$ $SO_2(C_1$–$C_6$ alkyl), $-NR^4SO_2$ aryl, $-NR^4CO(C_1$–$C_6$ alkyl), $-NR^4CO$ aryl or a 5 to 7-membered N-linked cyclic group incorporating W in the ring wherein W is O, $NR^5$, CH(OH), $CHCO_2H$, $CHN(R^4)_2$, CHF, $CF_2$, C=O or $CH_2$; $R^4$ is H or $C_1$–$C_6$ alkyl; $R^5$ is H, $C_1$–$C_6$ alkyl, $C_3$–$C_7$ cycloalkyl, $C_3$–$C_7$ cycloalkyl($C_1$–$C_6$)alkyl, $C_2$–$C_6$ alkanoyl, $C_4$–$C_8$ cycloalkanoyl, $C_3$–$C_7$ cycloalkyl($C_2$–$C_6$)alkanoyl, aryl CO—, $C_1$–$C_6$ alkyl $SO_2$—, $C_3$–$C_7$ cycloalkyl $SO_2$—, $C_3$–$C_7$ cycloalkyl ($C_1$–$C_6$)alkyl $SO_2$—, aryl-$SO_2$— or $(R^6)_2NSO_2$—, wherein each $R^6$ is independently H or $C_1$–$C_4$ alkyl or the two groups may be joined to form with the nitrogen atom to which they are attached, a pyrrolidinyl, piperidino, morphlino or piperazinyl group; m is 0, 1 or 2 with the proviso that m is not 0 when W is $NR^5$, C=O, or O; and n is an integer of from 1 to 4; are neurokinin receptor antagonists of utility in the treatment of a variety of medical conditions including urinary incontinence, asthma and related conditions.

9 Claims, No Drawings

3-AZA AND 3-OXA PIPERIDONE TACHYKININ ANTAGONISTS

This invention relates to certain 3-aza and 3-oxa-piperidone derivatives which are neurokinin receptor antagonists of utility in the treatment of a variety of medical conditions including, for example, asthma and urogenital tract disorders. More particularly this invention relates to certain 5-aryl-5-(1-azetidinylalkyl)-N-substituted-3-aza and 3-oxa-piperidone derivatives, to processes for their preparation, compositions thereof and their use in medicine.

According to the specification of our co-pending International patent application PCT/EP95/03054 we describe and claim a series of 5-aryl-5-azetidinylalkyl-piperidone derivatives. The compounds are antagonists of tachykinins, including neurokinin A, neurokinin B and Substance P, acting at the human neurokinin-1 ($NK_1$), neurokinin-2 ($NK_2$) or neurokinin-3 ($NK_3$) receptor, and are therefore potentially useful for preventing or treating a variety of medical conditions in which these receptors have been implicated, including inflammatory diseases such as arthritis, psoriasis, asthma or inflammatory bowel disease; central nervous system disorders such as anxiety, depression, dementia or psychosis; gastro-intestinal disorders such as functional bowel disease, irritable bowel syndrome, gastro-oesophageal reflux, faceal incontinence, colitis, Crohn's disease or diseases caused by *Helicobacter pylori* or other bacteria; urogenital tract disorders such as incontinence, hyperreflexia, impotence or cystitis; pulmonary disorders such as chronic obstructive airways disease; allergies such as eczma, contact dermatitis, atopic dermatitis, urticaria, rhinitis or hypersensitivity disorders such as to poison ivy; vasospastic diseases such as angina or Reynaud's disease; proliferative disorders such as cancer or a disorder involving fibroblast proliferation; fibrosing or collagen diseases such as scleroderma or eosinophillic fascioliasis; reflux sympathetic dystrophy such as shoulder/hand syndrome; addiction disorders such as alcoholism; stress-related somatic disorders; peripheral neuropathies such as diabetic neuropathy, neuralgia, causalgia, painful neuropathy, burns, herpetic neuralgia or post herpetic neuralgia; neuropathological disorders such as Alzheimer's disease or multiple sclerosis, disorders related to immune enhancement or suppression such as systemic lupus erythematosis; rheumatic diseases such as fibrositis or emesis; opthalmic diseases such as retinopathy; viral diseases such as colds and influenza; cough;acute or chronic pain or migraine.

The present invention provides a further series of related 3-aza and 3-oxa-piperidone derivatives. The compounds are potent and selective antagonists of tachykinins including neurokinin A, neurokinin B and substance P, active at the human $NK_1$, $NK_2$ and $NK_3$ receptors and they thus have potential utility in any of the disease states indicated above including, in particular treating or preventing inflammatory diseases such as arthritis, psoriasis, asthma or inflammatory bowel disease; central nervous system disorders such as anxiety, depression, dementia or psychosis; gastrointestinal disorders such as functional bowel disease, irritable bowel syndrome, gastro-oesophageal reflux, faecal incontinence, colitis or Crohn's disease; urogenital tract disorders such as incontinence or cysitiss; pulmonary disorders such as chronic obstructive airways disease; allergies such as eczema, contact dermatitis or rhinitis; hypersensitivity disorders such as to poison ivy; peripheral neuropathies such as diabetic neuropathy, neuralgia, causalgia, painful neuropathy, burns, herpetic neuralgia or post-herpetic neuralgia; cough or acute or chronic pain.

Thus, the present invention provides compounds having the formula:

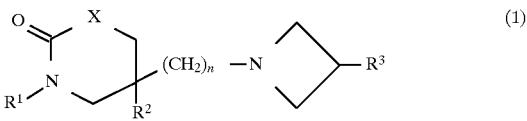

and pharmaceutically acceptable salts thereof, wherein:

X is O, NH or $NR^1$;

$R^1$ is $C_1$–$C_6$ alkyl, $C_3$–$C_7$ cycloalkyl, $C_3$–$C_7$ cycloalkyl($C_1$–$C_4$)alkyl, aryl, or aryl($C_1$–$C_4$)alkyl; wherein the $C_1$–$C_6$ alkyl group is optionally substituted by fluoro and the $C_3$–$C_7$ cycloalkyl or $C_3$–$C_7$ cycloalkyl($C_1$–$C_4$)alkyl group is optionally substituted in the cycloalkyl ring by up to two substituents each independently selected from halo, $C_1$–$C_4$ alkoxy or halo($C_1$–$C_4$)alkoxy;

$R^2$ is phenyl optionally substituted with one or two halo substituents, indolyl or thienyl;

$R^3$ is $NH_2$, —$NR^4SO_2(C_1–C_6$ alkyl), —$NR^4SO_2$ aryl, —$NR^4CO(C_1–C_6$ alkyl), —$NR^4CO$ aryl or a group of the formula:

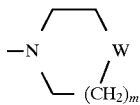

wherein W is O, $NR^5$, CH(OH), $CHCO_2H$, $CHN(R^4)_2$, CHF, $CF_2$, C=O or $CH_2$;

$R^4$ is H or $C_1$–$C_6$ alkyl;

$R^5$ is H, $C_1$–$C_6$ alkyl, $C_3$–$C_7$ cycloalkyl, $C_3$–$C_7$ cycloalkyl($C_1$–$C_6$)alkyl, $C_2$–$C_6$ alkanoyl, $C_4$–$C_8$ cycloalkanoyl, $C_3$–$C_7$ cycloalkyl($C_2$–$C_6$)alkanoyl, aryl CO—, $C_1$–$C_6$ alkyl $SO_2$—, $C_3$–$C_7$ cycloalkyl $SO_2$—, $C_3$–$C_7$ cycloalkyl($C_1$–$C_6$)alkyl $SO_2$—, aryl-$SO_2$— or $(R^6)_2NSO_2$—, wherein each $R^6$ is independently H or $C_1$–$C_4$ alkyl or the two groups may be joined, to form with the nitrogen atom to which they are attached, a pyrrolidinyl, piperidino, morpholino or piperazinyl group;

m is 0, 1 or 2 with the proviso that m is not 0 when W is $NR^5$, C=O, or O; and n is an integer of from 1 to 4.

In the above definitions of $R^1$, $R^3$ and $R^5$, aryl means phenyl optionally substituted by halo, $C_1$–$C_4$ alkyl, $C_1$–$C_4$ alkoxy, halo($C_1$–$C_4$)alkyl or halo($C_1$–$C_4$)alkoxy, and halo means fluoro, chloro, bromo or iodo. Alkyl and alkoxy groups containing three or more carbon atoms may be straight or branched-chain.

The pharmaceutically acceptable salts of the compounds of the formula (I) include the acid addition and the base salts thereof. Suitable acid addition salts are formed from acids which form non-toxic salts; examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts. Suitable base salts are formed from bases which form non-toxic salts; examples are the aluminium, calcium, lithium, magnesium, potassium, sodium, zinc and diethanolamine salts.

The compounds of the formula (I) may contain one or more asymmetric carbon atoms and may therefore exist in two or more stereoisomeric forms. The present invention includes the individual stereoisomers of the compounds of the formula (I) and mixtures thereof. Separation of diastereoisomers may be achieved by conventional techniques, e.g. by fractional crystallisation or chromatography of a stereoisomeric mixture of a compound of the formula (I) or a suitable salt or derivative thereof.

Preferred examples of the compounds of the formula (I) are those wherein $R^1$ is cyclopropylmethyl or benzyl; $R^2$ is 3,4-dichlorophenyl, n is 2 and $R^3$ is morpholino, 4-methylsulphonylpiperazinyl, or 4-hydroxy-piperidino.

Particular and preferred examples of compounds of the invention include: 5-(3,4-dichlorophenyl)-1-(cyclopropylmethyl)-5-[3-(4-hydroxypiperidino)-azetidinylethyl-3-azapiperidin-2-one.

The compounds of the formula (I) provided by this invention can be prepared by reductive amination using as starting materials a compound of the formula:

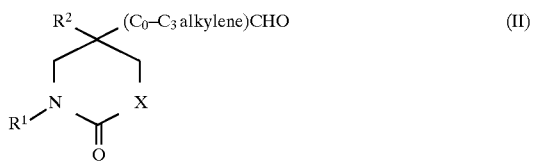

(II)

where $R^1$ and $R^2$ are as previously defined for a compound of the formula (I), and compound of the formula:

(III)

or an acid addition salt thereof, where $R^3$ is as previously defined for a compound of the formula (I). The reaction is preferably carried out in the presence of a suitable acid, e.g. acetic acid.

The reaction proceeds via the initial formation of an intermediate iminium salt of the formula:

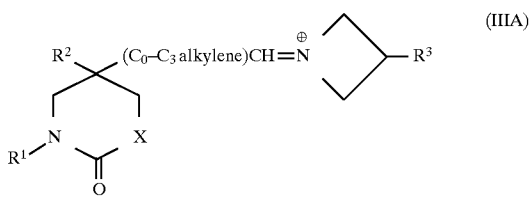

(IIIA)

which may be stable and isolatable. The reaction is preferably carried out without isolation of the intermediate of the formula (IIIA) in which case it is reduced in situ to provide a compound of formula (I).

In a typical procedure, an aldehyde of the formula (II) is first reacted with a compound of the formula (III) in a suitable solvent, e.g. tetrahydrofuran, and the mixture then treated with a suitable reducing agent, e.g. sodium triacetoxyborohydride or sodium cyanoborohydride, in the presence of a suitable acid, e.g. acetic acid, to give the required product. If an acid addition salt of a compound of the formula (III) is used as a starting material, a suitable acid acceptor, e.g. triethylamine, can be added prior to the addition of the reducing agent. The reaction is typically carried out at room temperature, and is generally substantially complete within 1 to 3 hours. The product is isolated and purified by conventional procedures e.g. by crystallisation or column chromatography.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The aldehyde starting materials of formula (II) may be prepared by a number of different routes depending on the nature of the X substituent.

(i) In one process, compounds of formula (II) wherein X is oxygen may be prepared according to the following reaction scheme:

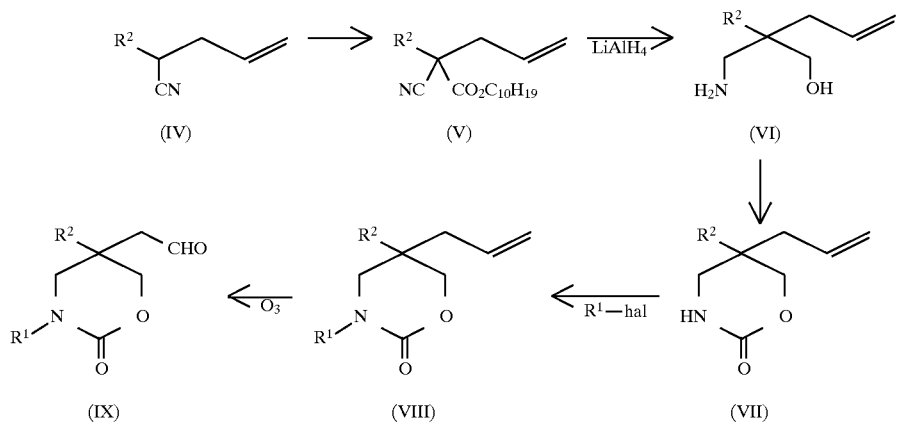

In the first step of this process, reaction of a 2-substituted pent-4-enenitrile (IV) with lithium diisopropylamide followed by reaction with (−) menthylchloroformate yields the (−)-menthyl-pent-5-enoate (V). Reduction with lithium aluminium hydride followed by cyclisation of the product (VI)

with N,N-disuccinimidyl carbonate yields the 3-oxapiperidone (VII). This is then N-alkylated by reaction with a halo compound of formula $R^1$-hal, where $R^1$ is as previously defined and hal is a halogen atom e.g. bromo, to give the product of formula (VIII). This is finally oxidised by ozonolysis to yield the 5-formylmethyl-3-oxapiperidine-2-one derivative (IX).

(ii) The corresponding 3-azapiperidine-2-one derivatives may be prepared by the following route:

The 3-substituted-azetidines of formula (Ill) are either known compounds or they are prepared by conventional procedures from known products following literature precedents.

All of the above reactions and the preparations of novel starting materials used in the preceding methods are conventional and appropriate reagents and reaction conditions for their performance or preparation as well as procedures for isolating the desired products will be well known to those

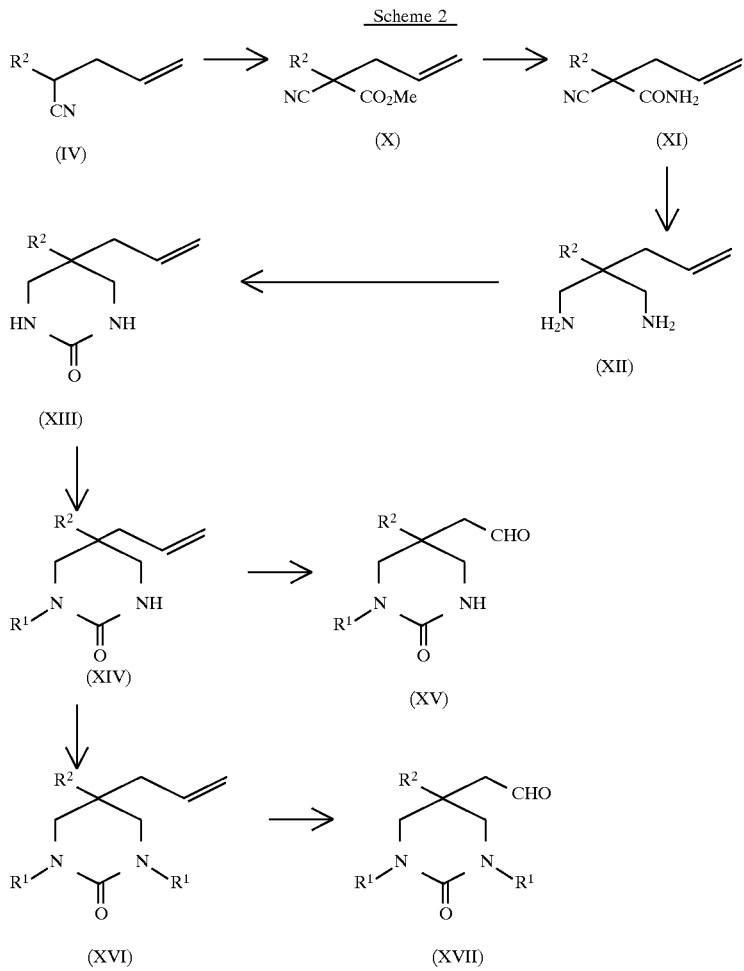

In this process the 2-substituted-pent-4-enenitrile (IV) is reacted with lithium diisopropylamide followed by methylchloroformate. The resulting compound of formula (X) is treated with concentrated ammonium hydroxide to yield the amide (Xl). Reduction with lithium aluminium hydride gives the diamine (XII) which is cyclised by reaction with 1,1-carbonyldiimidazole to yield the 3-azapiperidinone (XIII). This is then either mono-N-alkylated to give compounds of the formula (XIV) wherein X is NH or di-N-alkylated to give compounds of the formula (XVI) wherein both nitrogen atoms are subsituted. The process may be conducted in one step, in which case both $R^1$ groups are the same, or stepwise if it is desired that the $R^1$ groups be different. Finally the product (XIV) or (XVI) is oxidised by ozonolysis to yield the 5-formylmethyl-3-azapiperidin-2-one derivatives of formula (XV) or (XVII) respectively.

The above reactions can be performed starting with a different alkene-nitrile to yield the appropriate intermediates for the compounds of formula (I) wherein n is other than 2.

skilled in the art with reference to literature precedents and to the Examples and Preparations hereto.

The high activity of the compounds of the invention as neurokinin receptor antagonists is demonstrated by the following procedures:

The affinity of the compounds of formula (I) and their salts for the human $NK_1$ receptor can be tested in vitro by measuring their ability to inhibit [$^3$H]-Substance P binding to membranes prepared from the human IM9 cell line expressing the human $NK_1$ receptor using a modification of the method described in McLean, S. et al, J. Pharm. Exp. Ther., 267, 472–9 (1993) in which, instead of using whole cells, the cells are homogenised using a tissue homogeniser, and the particulate fraction is pelleted by centrifugation and washed three times with buffer prior to resuspension of the membranes.

The affinity of the compounds of formula (I) and their salts for the human $NK_2$ receptor can be measuring in vitro by testing their ability to compete with [$^3$H] or [$^{125}$I]NKA (neurokinin A) for binding to membranes prepared from Chinese hamster ovary cells expressing the cloned human NK$_2$ receptor. In this method, washed Chinese hamster ovary cell membranes are prepared as described for the previous method where IM9 cells are used instead. The membranes are incubated (90 min, 25° C.) with [$^{125}$I]NKA and a range of concentrations of the test compound. Non-specific binding was determined in the presence of 10 μM NKA.

The NK$_2$ receptor antagonist activity of the compounds of the formula (I) can also be measured, in vitro, by testing their ability to antagonise the contractile effects of the selective NK$_2$ receptor agonist [βAla$^8$]NKA$_{(4-10)}$ (Rovereo, P. et al, Neuropeptides, 13, 263–270, 1989) in the rabbit pulmonary artery, using the method of Patacchini and Maggi, Eur. J. Pharmacol., 236, 31–37 (1993).

The compounds of the formula (I) and their salts can be tested for NK$_2$ receptor antagonist activity, in vivo, by measuring their ability to inhibit bronchoconstriction induced by [βAla$^8$]NKA$_{(4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for NK$_3$ receptor antagonist activity, in vitro, by measuring their ability to antagonise the contractile effects of the selective NK$_3$ receptor agonist senktide in the guinea-pig ileum using the method of Maggi et al, Br. J. Pharmacol., 101, 996–1000 (1990).

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.5 to 5, and most preferably from 1 to 2, mg/kg (in single or divided doses). Thus tablets or capsules of the compounds will contain from 0.1 to 500, preferably from 50 to 200, mg of active compound for administration singly or two or more at a time, as appropriate. In any event, the physician will determine the actual dosage which will be most suitable for an individual patient and it will vary with the age, weight and response of the particular patient and disease being treated. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polythylene glycols or liquid paraffin; or they can be incorporated, at a concentration between 1 and 10%, into an ointment consisting of a white wax or white soft paraffin base together with such stabilizers and preservatives as may be required. Such formulations will be selected as appropriate to the particular disease being treated and mode of administration required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect on a tachykinin acting at the human NK$_1$, NK$_2$ or NK$_3$ receptor, or a combination thereof;

iv) use as in (iii) where the disease is an inflammatory disease such as arthritis, psoriasis, asthma or inflammatory bowel disease, a central nervous system disorder such as anxiety, depression, dementia or psychosis, a gastrointestinal disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain.

v) a method of treatment of a human to treat a disease by producing an antagonist effect on a tachykinin acting at the human NK$_1$, NK$_2$ or NK$_3$ receptor, or a combination thereof, which comprises treating said human with an effective amount of a compound of the formula (I) or with a pharmaceutically acceptable salt or composition thereof;

vi) a method as in (v) where the disease is an inflammatory disease such as arthritis, psoriasis, asthma or inflammatory bowel disease, a central nervous system disorder such as anxiety, depression, dementia or psychosis, a gastro-intestinal disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain;

The following Examples illustrate the preparation of the compounds of the formula (I) and the Preparations illustrate preparation of the intermediates of formulae (II) and (III).

EXAMPLE 1

5-(3,4-Dichlorophenyl)-1-(cyclohexylmethyl)-5-[2-(3-morpholinoazetidin-1-yl]ethyl)-3-oxapiperidin-2-one

Triethylamine (0.14 ml, 1 mmol) was added to a solution of 5-(3,4-dichlorophenyl)-1-cyclohexylmethyl-5-formylmethyl-3-oxapiperidin-2-one (see Preparation 1) (177 mg, 0.46 mmol) and 3-morpholinoazetidine dihydrochloride (119 mg, 0.54 mmol) in tetrahydrofuran (10 ml). After one hour, sodium triacetoxyborohydride (136 mg, 1.4 mol equivalent) was added, followed immediately by glacial acetic acid (26 μl, 1 equivalent) and the mixture stirred for 1½ hours. Saturated aqueous sodium bicarbonate solution (10 ml) was added and the mixture extracted with ethyl acetate (10 ml×2). The combined organic extracts were dried over magnesium sulphate and the solvent removed under reduced pressure. The residue was chromatographed using silica gel eluting with a solvent gradient of methanol:ethylacetate (1:10 to 40:60 by volume) to provide the title compound (174 mg). LRMS m/z=509 (M$^+$). TLC Rf=0.2 (silica, ethyl acetate:methanol, 9:1 by volume). Found: C,58.24; H,7.02, N,7.48. $C_{26}H_{37}N_3O_3Cl_2$. 0.4 $CH_2Cl_2$ requires C,58.24, H,7.00, N,7.72%. $^1$H-NMR (CDCl$_3$): δ=0.75–1.35(m,5H), 1.4–1 .5(m,1H), 1.5–1.9(m,7H), 2.1–2.4(m,6H), 2.7–2.8(m,2H), 2.8–3.0(m,1H), 3.05–3.3(m, 2H), 3.3–3.55(m,4H), 3.6–3.8(m,4H), 4.3–4.4(m,1H), 4.5–4.6(m,1H), 7.0–7.1 (m,1H), 7.25–7.3(m,1H), 7.35–7.45 (m,1H)ppm.

EXAMPLES 2–5

The following 3-azapiperidinones of formula (I) wherein X is NR$^6$, R$^2$ is 3,4-dichlorophenyl and n is 2 were prepared by a similar method to that used in Example 1 using the appropriate aldehyde derivative of preparations 2, 3A or 3B as starting material, and reacting with the appropriate 3-substituted azetidine.

| Example No | R$^1$ | R$^6$ | R$^3$ | LRMS m/z | Analysis/$^1$H-NMR |
|---|---|---|---|---|---|
| 2 (note 1) | Ph-CH$_2$— | Ph-CH$_2$— | —N(morpholine)O | 595 (M+H)$^+$ | Found: C, 66.16; H, 6.24; N, 9.05. $C_{33}H_{38}Cl_2N_4O_2$·0.084 $CH_2Cl_2$ requires C, 66.14, N, 6.40, N, 9.33%. $^1$H-NMR(CDCl$_3$): δ =1.5–1.65 (m,2H), 1.8–2.0(m, 2H), 2.15–2.25(m, 4H), 2.45–2.55(m, 2H), 3.7–3.9(m, 1H),3.2–3.4 (m, 6H),3.6–3.8(m, 4H), 4.4(d, 2H), 4.7(d, 2H), 6.6(d, 1H), 7.1–7.4(m, 12H). |
| 3 (note 2) | Ph-CH$_2$— | Ph-CH$_2$— | —N(piperazine)N—SO$_2$CH$_3$ | | Found: C,60.03; H, 6.04; N, 9.87. $C_{34}H_{41}Cl_2N_5O_3S$ requires C, 60.89, H, 6.13, N, 10.44%. $^1$H-NMR (CDCl$_3$): δ = 1.5–1.6(m, 2H), 1.85–2.0(m, 2H), 2.3–2.4(m, 4H) 2.5–2.6(m, 2H), 2.78(s, 3H), 2.8–3.0(m, 1H), 3.15–3.4(m, 10H), 4.4(d, 2H), 4.7(d, 2H), 6.6(d, 1H), 6.9(d, 1H, 7.1–7.4(m, 11H). |
| 4 (note 3) | cyclopropyl-CH$_2$— | cyclopropyl-CH$_2$— | —N(piperidine)—OH | 535 (M$^{30}$) | $^1$H-NMR(CDCl$_3$): δ = 0.3–0.4(m, 4H), 0.5–0.7(m, 4H), 0.9–1.1(m,2H), 1.5–3.4(m, 25H), 3.6–3.8(m, 2H), 7.3–7.4(m, 1H), 7.5–7.7(m, 2H). |
| 5 (note 4) | cyclopropyl-CH$_2$— | H | —N(piperidine)—OH | — | $^1$H-NMR(CDCl$_3$): δ = 0.2–0.3 (m,2H), 0.45–0.6(m, 2H), 0.8–1.0(m, 1H), 1.3–2.1(m, 9H), 2.1–2.3(m, 2H), 2.5–2.6(m, 2H), 2.6–2.8(m, 2H), 2.85–3.0(m, 1H), 3.1–3.8(m, 9H), 4.6(s, 1H), 7.1–7.2 (m, 1H), 7.4–7.5(m, 2H). |

Footnotes:
1. Chromatography using silica gel eluting with methanol dichloromethane (1:24 by volume).
2. Chromatography using silica gel eluting with methanol:dichloromethane (1:49 by volume).
3. Chromatography using silica gel eluting with methanol:dichloromethane (1:9 by volume).
4. Chromatography using silica gel eluting with methanoi:dichloromethane:ammonium hydroxide (10:89:1 by volume).

PREPARATION 1

5-(3,4-Dichlorophenyl)-1-cyclohexylmethyl-5-formylmethyl-3-oxapiperidin-2-one

(a) 2-(3,4-Dichlorophenyl)pent-4-enenitrile

A solution of 3,4-dichlorophenyl acetonitrile (200 g, 1.075 mol) in dry tetrahydrofuran (400 ml) was added dropwise, over one hour to sodium hydride 60% w/w dispersion in oil (32.26 g, 1.075 mole) in dry tetrahydrofuran (400 ml) at 0° C. under nitrogen. After a further thirty minutes the solution was cooled to −20° C. and a solution of allyl bromide (92.9 ml, 1 mol equivalent) in tetrahydrofuran (200 ml) was added, the mixture allowed to warm to room temperature and stirred for fourteen hours. Saturated brine (600 ml) was added and the mixture extracted with dichloromethane (2×600 ml). The organic layers were combined, dried over magnesium sulphate, and the solvent removed under reduced pressure. The residue was chromatographed on silica gel, eluting with a solvent gradient of ethyl acetate/hexane to provide the title compound as an oil (71.3 g). TLC Rf=0.71 (silica, diethylether:hexane, 1:1 by volume). $^1$H-NMR (CDCl$_3$): δ=2.6–2.75(m,2H), 3.85(t,1H), 5.1–5.25 (m,2H), 5.7–5.9(m,1H), 7.2–7.25(m,1H), 7.5–7.55(m,2H) ppm.

(b) (−)-Menthyl-2-cyano-2-(3,4-dichlorophenyl)pent-5-enoate n-Butyllithium (36.9 ml of a 2.5M solution in hexane; 1.05 mol equivalent) was added to a solution of diisopropylamine (14.56 ml, 105.4 mmol) in tetrahydrofuran (250 ml) at −78° C. under nitrogen and the solution was then allowed to warm to room temperature over 1 hour. The solution was cooled to −78° C. and a solution of the product from part (a) (14.86 g; 87.8 mmol) in tetrahydrofuran (50 ml) was added slowly. The resulting solution was allowed to warm to room temperature over 4 hours. The solution was then cooled to −78° C. and a solution of (−)-menthylchloroformate (25 g, 1.3 mol equivalent) in tetrahydrofuran (50 ml) added dropwise. The reaction was allowed to warm to room temperature and stirred for fourteen hours. The solution was then poured into water (500 ml) and extracted with t-butylmethylether (2×500 ml). The combined organic layers were dried over magnesium sulphate, and the solvent removed under reduced pressure. Chromatography using silica gel eluting with a solvent gradient of ethyl acetate:hexane (1:20 to 1:6, by volume) gave the product as a diasteromeric mixture (34.2 g). TLC Rf=0.2 (silica, ethyl acetate:hexane, 1:20 by volume, eluting twice). $^1$H-NMR (CDCl$_3$): δ=0.5(d,1H), 0.7(d,1H), 0.8–1.15(m, 6H), 1.2(d,2H), 1.3–1.5(m,2H), 1.6–1.8(m,3H), 1.75–1.85 (m,1H), 1.9–2.1 (m,1H), 2.7–2.85(m,1H), 3.0–3.1 (m,1H), 4.6–4.8(m,1H), 5.2–5.3(m,2H), 5.6–5.8(m,1H), 7.3–7.4(m, 1H), 7.4–7.5(m,1H), 7.6–7.7(m,1H)ppm.

(c) 2-(Aminomethyl)-2-(3,4-dichlorophenyl)-pent-5-enol

A solution of the above product (10.04 g; 1 mol equivalent) in tetrahydrofuran (40 ml) was added to a solution of lithium aluminium hydride (1.87 g, 49.2 mmol) in tetrahydrofuran (40 ml) at 0° C. under nitrogen. The mixture was then allowed to warm to room temperature and stirred for 4½ hours. Water (10 ml) was carefully added to the green coloured solution followed by 2N sodium hydroxide solution (2×10 ml). The resulting solid was collected by filtration and washed with t-butyl methyl ether (100 ml). The filtrate was then extracted using t-butyl methyl ether (2×100 ml). The organic extracts were combined, dried over magnesium sulphate, and the solvent removed under reduced pressure. Chromatography using silica gel eluting with a solvent gradient of ethyl acetate:methanol (1:50 to 2:25, by volume) gave the title compound (2 g). TLC Rf=0.2 (silica, methanol:ethyl acetate, 1:20, by volume). LRMS m/z=260.2 (M+H)$^+$.

(d) 5-Allyl-5-(3,4-dichlorophenyl)-1-(1H)-3-oxapiperidin-2-one

A solution of the above compound (2 g, 7.69 mmol) in dichloromethane (10 ml), and a solution of N,N-disuccinimidyl carbonate (2.95 g, 1.5 mol equivalent) in dichloromethane (10 ml) were added simultaneously over 20 minutes to a solution of triethylamine (3.2 ml, 23.07 mmol, 3 mol equivalent) in dichloromethane (10 ml) at 0° C., under nitrogen. The solution was allowed to warm to room temperature and stirred for 16 hours. The reaction mixture was washed with 2N hydrochloric acid and the organic layer separated, dried over magnesium sulphate and the solvent removed under reduced pressure. Chromatography using silica gel eluting with a solvent gradient of ethyl acetate to ethyl acetate:methanol (10:1 by volume), gave the title compound (0.6 g). TLC Rf=0.5 (silica, methanol:ethyl acetate, 1:20, by volume). LRMS m/z=286 (M$^+$). $^1$H-NMR (CDCl$_3$):δ=2.4–2.55(m,2H), 3.4–3.6(m,2H), 4.2–4.5(m, 2H), 4.9–5.1(m,2H), 5.2–5.4(m,1H), 6.2–6.4(m,1H), 7.0–7.05(m,1H), 7.2–7.4(m,2H).

(e) 5-Allyl-5-(3,4-dichlorophenyl)-1-cyclohexylmethyl-3-oxapiperidin-2-one

Potassium hydroxide (2.17 mg, 1.85 mol equivalent) was added to a solution of the above compound (600 mg, 2.1 mmol) in dimethyl sulphoxide (10 ml) and the mixture stirred at room temperature for 20 minutes. Bromomethylcyclohexane (409 mg, 1.1 mol equivalent) was added and the reaction mixture stirred for a further 3½ hours. The mixture was poured into brine (100 ml) and extracted with ethyl acetate (2×50 ml). The combined organic layers were washed with water (2×100 ml), dried over magnesium sulphate, and the solvent removed under reduced pressure. The residue was chromatographed using silica gel eluting with a solvent gradient of ethyl acetate:hexane (1:1 to 1:20, by volume) to provide the title compound (220 mg). TLC Rf=0.8 (silica, ethyl acetate). LRMS m/z=382(M$^+$). $^1$H-NMR (CDCl$_3$):=0.8–1.0(m,2H), 1.05–1.3(m,3H), 1.35–1.45(m,1H), 1.5–1.8(m,5H), 2.45(d,2H), 3.05–3.2(m, 2H), 3.4–3.6(m,2H), 4.4(dd,2H), 5.0–5.1(m,2H), 5.3–5.5(m, 1H), 7.05–7.1 (m,1H), 7.3–7.5(m,2H).

(f) 5-(3,4-Dichlorophenyl)-1-cyclohexylmethyl-5-formylmethyl-3-oxapiperidin-2-one Ozone was bubbled into a solution of the above compound (206 mg, 0.54 mmol) in methanol (12 ml) under nitrogen at −78° C. at a rate of 50 ml/minute (using a charge of 1.5 A to generate the ozone from oxygen) for thirty minutes. After this time the amperage was reduced to zero and oxygen bubbled through at a rate of 5 ml/minute for two minutes. The oxygen supply was then removed and nitrogen bubbled through the reaction mixture for twenty minutes. After this time a solution of dimethyl sulphide (0.5 ml) in methanol (2.5 ml) was cautiously added dropwise and the reaction left to warm over eighteen hours. The solvent was removed under reduced pressure and the reaction mixture was partitioned between ethyl acetate (30 ml) and water (2×25 ml). The organic layers were dried using magnesium sulphate, filtered and the filtrate evaporated to dryness under reduced pressure, to give the title compound (177 mg) which was used without further purification. TLC Rf=0.15 (silica, hexane:ethyl acetate,1:1 by volume). $^1$H-NMR (CDCl$_3$): δ=0.8–1.0(m,2H), 1.05–1.3(m,3H), 1.4–1.8(m,6H), 2.9(s, 2H), 3.1–3.3(m,2H), 3.55–3.7(m,2H), 4.4–4.55(m,2H), 7.1–7.15(m,1H), 7.4–7.5(m,2H), 9.6(s,1H) ppm.

PREPARATION 2

1-Benzyl-3-benzyl-5-(3,4-dichlorophenyl)-5-formylmethyl-3-azapiperidine-2-one (a) Methyl 2-cyano-2-(3,4-dichlorophenyl)-pent-5-enoate n-Butyllithium (38.97 ml of a 2.5M solution in hexane, 1.1 mol equivalent) was added to a solution of diisopropylamine (17.16 ml, 1.4 mol equivalent, 124.02 mmol) in tetrahydrofuran (200 ml) at −78° C. under nitrogen, and the solution was allowed to warm to room temperature over 30 minutes. The solution was then cooled to −78° C. and a solution of 2-(3,4-dichlorophenyl)pent-4-enenitrile (20.02 g, 1 mol equivalent) in tetrahydrofuran (100 ml) was added slowly. The resulting solution was allowed to warm to room temperature over 1 hour. The solution was then cooled to −78° C. and a solution of methylchloroformate (9.61 ml, 1.1 mol equivalent) in tetrahydrofuran (50 ml) was added dropwise. The reaction was allowed to warm to room temperature over 4½ hours. The solution was then poured into water (300 ml) and extracted using dichloromethane (300 ml). The organic layer was dried over magnesium sulphate and the solvent removed under reduced pressure. Chromatography using silica gel eluting with a solvent gradient of ethyl acetate:hexane (1:20 to 1:6, by volume) gave the title compound as part of a mixture of products which was used directly in the next step. TLC Rf=0.8 (silica, ethyl acetate:hexane; 1:5 by volume).

(b) 2-Cyano-2-(3,4-dichlorophenyl)-pent-5-enecarboxamide

The above product was added to an ammonium hydroxide solution (120 ml; specific gravity 0.880) at room temperature. The mixture was stirred at room temperature for 16 hours then dichloromethane (250 ml) was added. The organic layer was washed with water (2×250 ml), dried over magnesium sulphate, and the solvent removed under reduced pressure. The residue was chromatographed using silica gel eluting with a solvent gradient of ethyl acetate:hexane (1:5 to 2:3 by volume) to provide the title amide (8.31 g). TLC Rf=0.1 (silica, ethyl acetate:hexane, 1:5 by volume). $^1$H-NMR (CDCl$_3$): δ=2.7–2.8(m,1H), 3.0–3.2(m, 1H), 5.15–5.3(m,2H), 5.6–5.8(m,1H), 6.3(d,b,2H), 7.3–7.4 (m,2H), 7.6–7.65(m,1H)ppm.

(c) 2-(Aminomethyl)-2-(3,4-dichlorophenyl)-1-amino-pent-5-ene

Aluminium chloride (43.24 g, 5.3 mol equivalent) was added slowly portionwise, to a solution of lithium aluminium hydride (12.31 g, 5.3 mol equivalent) in diethyl ether (315 ml) at 0° C. under nitrogen, and the mixture stirred for 5 minutes. A solution of the product from step (b) above (16.53 g; 61.4 mmol; 1 mol equivalent) in diethyl ether (100 ml) and tetrahydrofuran (33 ml) was then added dropwise. The solution was allowed to warm to room temperature and stirred for 16 hours. The mixture was then cooled to 0° C. and 2N sodium hydroxide solution (10 ml) added carefully. Ethanol (5 ml) was added followed by tetrahydrofuran (40 ml) A second portion of 2N sodium hydroxide solution (12 ml) was added and the mixture was stirred for 15 minutes, 12N sodium hydroxide (50 ml) was then added dropwise to the reaction mixture, together with additional tetrahydrofuran (200 ml). The mixture was stirred for 165 minutes and filtered using a filter aid. The filtrate was evaporated to provide crude material (6.9 g). Chromatography using silica gel eluting with a solvent gradient of methanol:dichloromethane: ammonium hydroxide (1:3:0 to 10:89.1) gave the title compound (2.03 g). TLC Rf 0.35 (silica, methanol:dichloromethane:ammonium hydroxide, 89:10:1, by volume).

(d) 5-Allyl-5-(3,4-Dichlorophenyl)-1-(1H)-3-azapiperidin-2-one

Into dichloromethane (300 ml) under nitrogen at room temperature was added dropwise simultaneously, a solution of the above compound (2.03 g) in dichloromethane (10 ml) and a solution of 1,1-carbonyldiimidazole (1.52 g) in dichloromethane (10 ml). Once the addition was complete the mixture was stirred for sixteen hours. The solvent was then removed and the residue chromatographed on silica gel eluting with methanol:dichloromethane (1:9, by volume) to provide the title compound (1.86 g). TLC Rf=0.4 (silica, methanol:dichloromethane 1:9 by volume). LRMS m/z 285 (M$^+$).

(e) 5-Allyl-1-benzyl-3-benzyl-5-(3,4-dichlorophenyl)-3-azapiperidin-2-one

Sodium hydride as a 60% w/v dispersion in oil (900 mg; 10 mol equivalent) was added to a solution of the above compound (670 mg; 2.35 mmol) in dimethylformamide (15 ml) under an atmosphere of nitrogen at 0° C. The mixture was stirred for 90 minutes and allowed to warm to room temperature. The mixture was then cooled to 0° C. and benzyl bromide (1.4 ml; 1 mol equivalent) added. The mixture was allowed to warm to room temperature and stirred for eighteen hours. Water (30 ml) was added carefully, and the mixture extracted using ethyl acetate (3×30 ml). The combined organic extracts were washed with water (20 ml), dried using magnesium sulphate, filtered and evaporated to dryness under reduced pressure. Chromatography using silica gel eluting with a solvent gradient of hexane:diethyl ether (1:1 by volume) provided the title compound (415 mg). $^1$H-NMR (CDCl$_3$): δ1.2–1.4(m,1H), 2.2–2.35(m,2H), 3.3–3.5(m,3H), 4.4–4.5(m,2H), 4.8–5.0(m, 4H), 5.1–5.3(m,1H), 6.6–6.7(m, 1H), 7.2–7.5(m,12H).

(f) 1-Benzyl-3-benzyl-5-(3,4-dichlorophenyl)-5-formylmethyl-3-azapiperidin-2-one The above product was oxidised following the general procedure of Preparation 1 step (f) to yield the title compound as an oil (420 mg). LRMS m/z 467(M$^+$). $^1$H-NMR (CDCl$_3$): δ=2.7(s,2H), 3.4–3.6(m,4H), 4.5–4.75(m,4H), 6.7–6.8(m,1H), 7.1 –7.4(m,12H), 9.2(s,1H).

PREPARATIONS 3A AND 3B (A) 5-(3,4-Dichlorophenyl)-1-cyclopropylmethyl-3(1H)-5-formylmethyl-3-azapiperidin-2-one (B) 5-(3,4-dichlorophenyl)-1-cyclopropylmethyl-3-cyclopropylmethyl-5-formylmethyl-3-azapiperidin-2-one (a) Potassium hydride as a 35% w/v dispersion in mineral oil (161 mg, 1 mol equivalent) was added to a solution of 5-allyl-5-(3,4-dichlophenyl)-1-(1H)-3-azapiperidin-2-one (Preparation 2, part (d); 400 mg, 1.4 mmol) in dimethylacetamide (20 ml) under an atmosphere of nitrogen at 0° C. The mixture was allowed to warm to room temperature and stirred for four hours. Cyclopropylmethyl bromide (0.14 ml; 1 mol equivalent) was added and the reaction left stirring for eighteen hours. The reaction mixture was then partitioned between ethyl acetate (30 ml) and water (20 ml). The ethyl acetate layer was separated, washed with water (4×20 ml), dried using sodium sulphate, fitered and evaporated to dryness under reduced pressure. The resulting mixture was chromatographed using silica gel eluting with methanol:dichloromethane (1:19 by volume) to provide the monosubstituted product A (119 mg) and the disubstituted product B (112 mg).

A) 5-Allyl-5-(3,4-dichlorophenyl)-1-cyclopropylmethyl-3(1H)-3-azapiperidin-2-one TLC Rf=0.4 (silica, methanol:dichloromethane 1:9 by volume). $^1$H-NMR (CDCl$_3$)=0.2–0.3(m,2H), 0.45–0.6(m, 2H), 0.8–1.0(m,1H), 2.4–2.5(m,2H), 3.1–3.6(m,6H), 4.8–5.1 (m,3H), 5.3–5.45(m,1H), 7.1–7.2(m,1H), 7.3–7.5 (m,2H).

B) 5-Allyl-1-(3,4-dichlorophenyl)-1-cyclopropylmethyl-3-cyclopropylmethyl-3-azapiperidin-2-one TLC Rf=0.53 (silica, methanol:dichloromethane, 1:9 by volume). $^1$H-NMR (CDCl$_3$)=0.1–0.3(m,4H), 0.4–0.6(m, 4H), 0.8–1.0(m,2H), 2.4–2.5(m,2H), 3.1–3.4(m,6H), 3.5–3.7(m,2H), 4.95–5.05(m,2H) , 5.3–5.45(m,1H), 7.1–7.2 (m,1H), 7.3–7.5(m,2H).

b) The above products were oxidised following the general procedure of

Preparation 1, step (f) to yield:

(A) 5-(3,4-Dichlorophenyl)-1-cyclopropylmethyl-5-formylmethyl-3-azapiperidin-2-one.

$^1$H-NMR (CDCl$_3$): δ=0.2–0.4(m,2H), 0.4–0.7(m,2H), 0.8–1.1(m,1H), 2.6–4.0(m,9H), 7.0–7.5(m,3H), 9.6(s,1H).

(B) 5-(3,4-Dichlorophenyl)-1-cyclopropylmethyl-3-cyclopropylmethyl-5-formylmethyl-3-azapiperidin-2-one.
$^1$H-NMR (CDCl$_3$): δ=0.1–0.7(m,8H), 0.8–1.0(m,4H), 2.8–4.0(m,8H), 7.0–7.5(m,3H), 9.6(s,1H).

PREPARATION 4

3-Morpholinoazetidine Dihydrochloride (a) 1-Diphenylmethylazetidin-3-ol

A solution of benzhydrylamine (200 ml, 1.6 mol) and epichlorohydrin (186 ml, 1 mol equivalent) in methanol (600 ml) was stirred at room temperature for five days and then heated at 40° C. for two days. The solvent was then removed under reduced pressure, the residue dissolved in isopropyl alcohol (500 ml) and the solution heated under reflux for six hours. The solution was cooled to room temperature and the precipitate filtered off. This solid was partitioned between dichloromethane (400 ml) and saturated aqueous sodium bicarbonate solution (500 ml). The aqueous phase was extracted with dichloromethane (2×400 ml), the combined organic extracts dried over magnesium sulphate, filtered and the solvent evaporated under reduced pressure to give the title product (86 g) as a crystalline solid. $^1$H-NMR (CDCl$_3$): δ=1.8–2.3(s,br,1H), 2.85–2.9(m,2H), 3.5–3.55(m, 2H), 4.35(s,1H), 4.4–4.5(m, 1H), 7.15–7.4(m,10H)ppm.

(b) 1-Diphenylmethyl-3-methanesulphonyloxyazetidine

Triethylamine (57 ml, 1.5 mol equivalent) was added to a solution of 1-diphenylmethylazetidin-3-ol (65.9 g, 275.7 mmol) in dry dichloromethane (700 ml) at 0° C. under nitrogen. After five minutes, methanesulphonyl chloride (25.6 ml, 1.2 mol equivalent) was added and the mixture stirred for one hour. Water (300 ml) was added and the mixture extracted with dichloromethane (3×300 ml). The combined organic layers were dried over magnesium sulphate and the solvent removed under reduced pressure. The residue was chromatographed on silica gel eluting with methanol:dichloromethane (1.49, by volume) to give the title product (73.4 g) as a solid. $^1$H-NMR (CDCl$_3$): δ=2.95 (s,3H), 3.15–3.25(m,2H), 3.6–3.65(m,2H), 4.4(s,1H), 5.05–5.15(m,1H), 7.15–7.4(m,10H)ppm.

(c) 1-Diphenylmethyl-3-morpholinoazetidine

A solution of the above product (24.46 g, 7.72 mmol), potassium carbonate (32 g, 3 mol equivalent) and morpholine (7.34 ml, 1.09 mol equivalent) in acetonitrile (200 ml) was heated under reflux for four hours. The solution was cooled to room temperature, water (50 ml) added and the mixture concentrated under reduced pressure. The residue was partitioned between ethyl acetate (400 ml) and water (400 ml) and the organic phase separated and washed with water (2×400 ml). The organic phase was dried over magnesium sulphate, filtered and the solvent removed under reduced pressure. The residue was chromatographed on silica gel eluting with hexane:diethyl ether (1:1, by volume) to give the title compound (16.5 g). $^1$H-NMR (CDCl$_3$): δ=2.25–2.3(m,4H), 2.85–3.05(m,3H), 3.35–3.4(m,2H), 3.7–3.75(m,4H), 4.45(s,1H), 7.15–7.45(m,10H)ppm.

(d) 3-Morpholinoazetidine dihydrochloride

A mixture of the above product (18.6 g, 60.4 mmol), palladium hydroxide (2 g), ethanol (200 ml) and 1 N aqueous hydrochloric acid (52 ml) was stirred under an atmosphere of hydrogen at 345 kPa (50 p.s.i.) for three days. The catalyst was removed by filtration and the filtrate evaporated to dryness. Addition of dichloromethane (100 ml) to the residue and trituration yielded a solid which was recrystallised from methanol to give the title compound (10.2 g) as a crystalline solid. LRMS m/z=179(m+1)$^+$.

PREPARATION 5

3-(4-Methylsulphonylpiperazin-1-yl)azetidine bistrifluoroacetate (a) 1-(Tert-butoxycarbonyl)-3-(1-piperazinyl)azetidine Piperazine (23.69 g, 8 mol equivalent) was melted and 1-(t-butoxycarbonyl)-3-methanesulphonyloxyazetidine (see International Patent Application Publication no WO93/19059; 8.64 g, 34.4 mmol) added. The mixture was heated at 120° C. for 15 hours under nitrogen. The reaction was cooled to room temperature and the excess piperazine removed under reduced pressure. The residue was chromatographed on silica gel using gradient elution (methanol:dichloromethane 1:19 changing to 1:4, by volume) to give the title compound (6.32 g). LRMS m/z= 242 (m+1)$^+$. $^1$H-NMR (d$_6$-DMSO): δ=1.35(s,9H), 2.4–2.5 (m,4H), 3.0–3.1 (m,5H), 3.2–4.2(m,br.,5H)ppm.

(b) 1-(Tert-butoxycarbonyl)-3-(4-methylsulphonyliperazin-1-yl)azetidine

To a solution of the above product (8.06 g, 21.3 mmol) in dichloromethane (160 ml) was added triethylamine (13.4 ml). The solution was kept under a nitrogen atmosphere and cooled to 0° C. Methanesulphonyl chloride (5.25 ml, 7.77 g, 3 mol equivalent) was added, dropwise, over 30 minutes. The reaction was allowed to warm to room temperature over 2.5 hours and then stirred for a further 18 hours. The reaction was washed with water (3×50 ml) and then brine (2×30 ml). The organic layer was dried using anhydrous magnesium sulphate, filtered and the solvent removed under reduced pressure. The residue was chromatographed on silica gel eluting with concentrated aqeuous ammonia:methanol:dichloromethane (1:10:89, by volume), followed by chromatography on silica gel eluting with methanol:ethyl acetate (1:10, by volume), to give the title compound (0.9 g). TLC Rf=0.6 (silica, concentrated aqueous ammonia solution:methanol:dichloromethane, 1:10:89 by volume). LRMS m/z=320(m+1)$^+$. $^1$H-NMR (CDCl$_3$): δ=1.4(s,9H), 2.45(t,4H), 3.8(s,3H), 3.1–3.2(m,1H), 3.2–3.3(m,4H), 3.75–3.8(m,2H), 3.9–4.0(m,2H)ppm.

(c) 3-(4-Methylsulphonylpiperazin-1-yl)azetidine bistrifluoroacetate

The above product in dichloromethane, was treated at 0° C. with trifluoroacetic acid to yield the title compound as a white solid. LRMS m/z 220 (m+1)$^+$. $^1$H-NMR (d$_6$-DMSO): δ=2.4–2.5(m,2H), 2.9(s,3H), 3.1–3.2(m,4H), 3.3–3.5(m, 1H), 3.8–4.0(m,4H), 8.7–8.9(m,3H)ppm.

PREPARATION 6

3-(4-Hydroxypiperidyl)azetidine bistrifluoroacetate a) A mixture of 1-(t-butoxycarbonyl)-3-methanesulphonyloxyazetidine (see International Patent Application Publication no WO93/19059) (1.2 g, 4.78 mmol) and 4-hydroxypiperidine (2.89 g, 6 mol equivalent) was heated at 110° C. for sixteen hours. The mixture was cooled to room temperature and partitioned between ethyl acetate (100 ml) and 5% aqueous sodium bicarbonate solution (100 ml). The layers were separated and the aqueous phase was extracted with a further portion of ethyl acetate (100 ml). The combined organic layers were dried over anhydrous magnesium sulphate. The solution was filtered, the solvent removed from the filtrate under reduced pressure and the crude product purified by column chromatography using silica gel eluting with methanol:dichloromethane (1:9, by volume) to give 1-butoxycarbonyl)-3-(4-hydroxypiperidyl)azetidine (1.4 g). TLC Rf=0.3 (silica, methanol:dichloromethane, 1:9, by volume). $^1$H-NMR (CDCl₃): δ=1.35–1.5(m,1OH), 1.55–1.65(m,2H), 1.9–2.1 (m,4H), 2.6–2.7(m,2H), 3.0–3.1 (m,1H), 3.7–3.95(m,5H) ppm.

b) Trifluoroacetic acid (5 ml), was added dropwise to a solution of the above compound (1.4 g, 5 mmol) in dichloromethane (10 ml) at 0° C. under nitrogen. The mixture was allowed to warm to room temperature and stirred for one hour. The mixture was concentrated under reduced pressure, the resulting gum washed with diethyl ether, triturated with diethyl ether and the solid collected by filtration to give the title compound as a white solid (1.45 g). Found: C,36.88; H,4.67; N,6.93. $C_8H_{16}N_2O$. $2CF_3CO_2H$ requires C,37.51; H,4.72; N,7.29%.

We claim:

1. A compound having the formula:

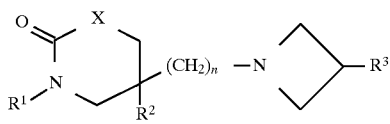

or a pharmaceutically acceptable salt thereof, wherein:

X is O, NH or $NR^1$;

$R^1$ is $C_1$–$C_6$ alkyl, $C_3$–$C_7$ cycloalkyl $C_3$–$C_7$ cycloalkyl ($C_1$–$C_4$)alkyl, aryl,or aryl($C_1$–$C_4$)alkyl; wherein the $C_1$–$C_6$ alkyl group is optionally substituted by fluoro and the $C_3$–$C_7$ cycloalkyl or $C_3$–$C_7$ cycloalkyl($C_1$–$C_4$)alkyl group is optionally substituted in the cycloalkyl ring by up to two substituents each independently selected from halo, $C_1$–$C_4$ alkoxy or halo($C_1$–$C_4$) alkoxy; and aryl means phenyl optionally substituted by halo, $C_1$–$C_4$alkyl, $C_1$–$C_4$ alkoxy, halo($C_1$–$C_4$ )alkyl or halo($C_1$–$C_4$ )alkoxy, $R^2$ is phenyl optionally substituted with one or two halo substituents, indolyl or thienyl;

$R^3$ is $NH_2$, —$NR^4SO_2(C_1$–$C_6$ alkyl), —$NR^4SO_2$ aryl, —$NR^4CO(C_1$–$C_6$alkyl), —$NR^4CO$ aryl or a group of the formula:

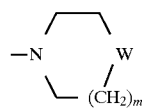

wherein W is O, $NR^5$, CH(OH), $CHCO_2H$, $CHN(R^4)_2$, CHF, $CF_2$, C=O or $CH_2$ and aryl is as previously defined;

$R^4$ is H or $C_1$–$C_6$ alkyl;

$R^5$ is H, $C_1$–$C_6$ alkyl, $C_3$–$C_7$ cycloalkyl, $C_3$–$C_7$ cycloalkyl ($C_1$–$C_6$ )alkyl, $C_2$–$C_6$ alkanoyl, $C_4$–$C_8$ cycloalkanoyl, $C_3$–$C_7$ cycloalkyl($C_2$–$C_6$ )alkanoyl, aryl CO—, $C_1$–$C_6$ alkyl $SO_2$—, $C_3$–$C_7$ cycloalkyl $SO_2$—, $C_3$–$C_7$ cycloalkyl($C_1$–$C_6$ )alkyl $SO_2$—, aryl-$SO_2$- or $(R^6)_2NSO_2$—, wherein each $R^6$ is independently H or $C_1$–$C_4$ alkyl or the two groups may be joined, to form with the nitrogen atom to which they are attached, a pyrrolidinyl, piperidino, morpholino or piperazinyl group and aryl is as previously defined;

m is 0, 1 or 2 with the proviso that m is not 0 when W is $NR^5$, C=O, or O;

and n is an integer of from 1 to 4.

2. A compound as claimed in claim 1 wherein $R^1$ is cyclopropylmethyl or benzyl.

3. A compound as claimed in claim 2 wherein $R^2$ is 3,4-dichlorophenyl.

4. A compound as claimed in claim 1 wherein n is 2.

5. A compound as claimed in claim 1 wherein $R^3$ is morpholino, 4-methylsulphonylpiperazinyl or 4-hydroxy-piperidino.

6. The compound 5-(3,4-dichlorophenyl)-1-(cyclopropylmethyl)-5-[3-(4-hydroxypiperidino)-azetidinylethyl]-3-azapiperidin-2-one.

7. A process for preparing a compound having the formula (I) as defined in claim 1 by reductive amination of a compound of the formula:

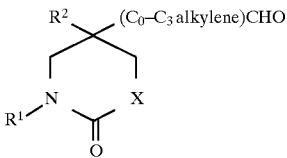

where $R^1$, $R^2$ and X are as previously defined for a compound of the formula (I), and a compound of the formula:

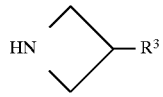

or an acid addition salt thereof, where $R^3$ is as previously defined for a compound of the formula (I), in the presence of a reducing agent and optionally in the presence of an acid.

8. A pharmaceutical composition comprising a compound of the formula (I) as claimed in claim 1, or a pharmaceutically acceptable salt thereof, together with a pharmaceutically acceptable diluent or carrier.

9. A method of treatment of a human for treating inflammatory diseases, arthritis, psoriasis, asthma or inflammatory bowel disease; central nervous system disorders, anxiety, depression, dementia or psychosis; gastro-intestinal disorders, functional bowel disease, irritable bowel syndrome, gastro-oesophageal reflux, faecal incontinence, colitis or Crohn's disease; urogenital tract disorders, incontinence or cystisis; pulmonary disorders, chronic obstructive airways disease; allergies, eczema, contact dermatitis or rhinitis; hypersensitivity disorders, poison ivy; peripheral neuropathies, diabetic neuropathy, neuralgia, causalgia, painful neuropathy, burns, herpetic neuralgia or post-herpetic neuralgia; cough or acute or chronic pain which comprises treating said human with an effective amount of a compound of the formula (I) or with a pharmaceutically acceptable salt thereof as claimed in claim 1.

* * * * *